US00PP18132P2

(12) United States Plant Patent
Brown, Jr.

(10) Patent No.: US PP18,132 P2
(45) Date of Patent: Oct. 16, 2007

(54) ***PERSICARIA* PLANT NAMED 'DRAGON'S EYE'**

(50) Latin Name: ***Persicaria (microcephala*×unknown)**
Varietal Denomination: Dragon's Eye

(75) Inventor: Kenneth E. Brown, Jr., Tigard, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/452,878

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct cultivar of *Persicaria* plant characterized by multicolored leaves exhibiting a large, striking brownish black triangular basal spot surrounded by a silvery olive chevron and trimmed with olive green edges.

1 Drawing Sheet

Botanical classification: *Persicaria* (*microcephala*×unknown).
Variety denomination: 'Dragon's Eye'.

BACKGROUND OF THE INVENTION

The present invention relates to a new and distinct cultivar of an herbaceous perennial of the genus, *Persicaria,* and known by the cultivar name of 'Dragon's Eye'. The genus *Persicaria* is a member of the family Polygonaceae.

The new cultivar is a seedling of *Persicaria microcephala* 'Red Dragon' (U.S. Plant Pat. No. 12,062). It was found among thousands of seedlings in a neighborhood backyard. As we believe that the original *P. m.* 'Red Dragon' is really a hybrid of *Persicaria microcephala,* no species designations are given.

SUMMARY OF THE INVENTION

This new cultivar is characterized by:

1) Foliage with striking markings and colors. Leaves are olive on the edges, silver in a chevron pattern, and brownish black in the large triangular basal spot.
2) Small leaves.
3) Spreading habit.

The new variety has been reproduced only by asexual propagation (cutting and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a close up of *Persicaria* 'Dragon's Eye' in the spring in Canby, Oreg.

FIG. 2 shows a one year old plant growing in the garden in summer in Canby, Oreg.

FIG. 3 shows a two year old plant in the fall in Canby, Oreg.

DETAILED PLANT DESCRIPTION

The following is a detailed description of the new cultivar based on observations of one and a half-year-old specimens growing in late September in the trial garden in Canby, Oreg. The color descriptions are all based on The Royal Horticultural Society Colour Chart.

Botanical name: *Persicaria* (*microcephala*×unknown).
Cultivar name: 'Dragon's Eye'.
Plant:
- *Form.*—Open, weaving mound.
- *Hardiness.*—USDA Zones 5 to 9.
- *Size.*—60 cm tall and 75 cm wide.
- *Habit.*—Clumping.

Stem:
- *Type.*—Succulent, with swollen nodes and sheath-like membranous stipules.
- *Size.*—2.5 mm above the third node down from the tip, 4 mm at plant base.
- *Internode spacing.*—3 to 5 cm.
- *Surface.*—Glabrous.
- *Color.*—Dark purple red. Greyed Purple 187C.

Leaf:
- *Type.*—Simple.
- *Arrangement.*—Alternate.
- *Shape.*—Ovate.
- *Venation.*—Pinnate.
- *Margins.*—Minutely denticulate and slightly undulate.
- *Apex.*—Accuminate to cuspidate.
- *Base.*—Truncate with two prominent basal lobes (perpendicular to the petiole, together 1.6 cm wide).
- *Size.*—5 to 8.2 cm long and 2.2 to 4 cm wide.
- *Vestiture.*—Sparsely pubescent.
- *Aspect.*—Matte.
- *Texture.*—Papery.

*Petiole length.*—0.5 to 1 cm and clasping at base.

*Petiole and major vein color.*—Greyed Purple 187C to A on top side to Greyed Purple 187D on bottom side.

*Leaf color.*—Variable depending on the light intensity. Mature leaves topside: Brown purple edged (between Brown 200B and Greyed Purple 187A) with an olive green chevron (closest to Greyed Green 191A). Mature leaves bottom side: Greyed Green 191B with red purple veins, Greyed Purple 185A and suffused with pink, Greyed Purple 185B. New leaves topside: Darker and pinker overall.

Inflorescence:

*Type.*—Terminal compound corymbs.

*Number of flowers.*—65 to 100 per corymb.

*Corymb size.*—Variable. 5.5 cm wide and 4 cm deep without peduncle.

*Peduncle.*—Length — 6 to 6.5 cm. Diameter — 1.5 mm. Texture — Glabrous. Color — Greyed Orange 176A.

*Pedicel.*—Texture — Pubescent. Color — Greyed Orange 177A.

*Bloom period.*—August to frost in Canby, Oreg.

Flower bud:

*Size.*—3 mm deep and 2 mm wide.

*Description.*—Ovoid.

*Color.*—White 155A with Greyed Purple 183C at base.

Flower:

*Type.*—Perfect, actinomorphic.

*Shape.*—Campanulate.

*Size.*—2.5 mm deep and 3 mm wide.

*Petal lobes.*—5, overlapping.

*Petal color.*—White 155A suffused with Greyed Purple 183C on bottom half.

*Petal texture.*—Waxy, thick.

*Calyx.*—Scarious, 0.5 mm deep and wide.

*Calyx color.*—Greyed Orange 177D.

*Stamen number.*—8.

*Filaments.*—White 155D.

*Anther color.*—Purple 77A.

*Pollen color.*—White 155D.

*Pistil color.*—White 155D.

*Pistil.*—Three branched style, 3 capitulate stigmas.

*Fragrance.*—None.

*Lastingness.*—Each corymb blooms for about 3 weeks on the plant.

Fruit: Never seen.

Seed: Never seen.

Disease and pest resistance and tolerance: *Persicaria* as a genus are susceptible to aphids, slugs and snails. No insect or diseases have been noted on *Persicaria* 'Dragon's Eye'.

Comparison to similar *Persicaria:* Compared to its parent *Persicaria* 'Red Dargon' (U.S. Plant Pat. No. 12,062), *Persicaria* 'Dragon's Eye' is shorter and more branched with smaller and more strongly marked leaves. Both have red purple stems and are weavers in habit.

I claim:

1. A new and distinct hybrid of *Persicaria* plant substantially as shown and described, characterized by multicolored leaves exhibiting a large, striking brownish black triangular basal spot surrounded by a silvery olive chevron and trimmed with olive green edges.

* * * * *

*Figure 1*
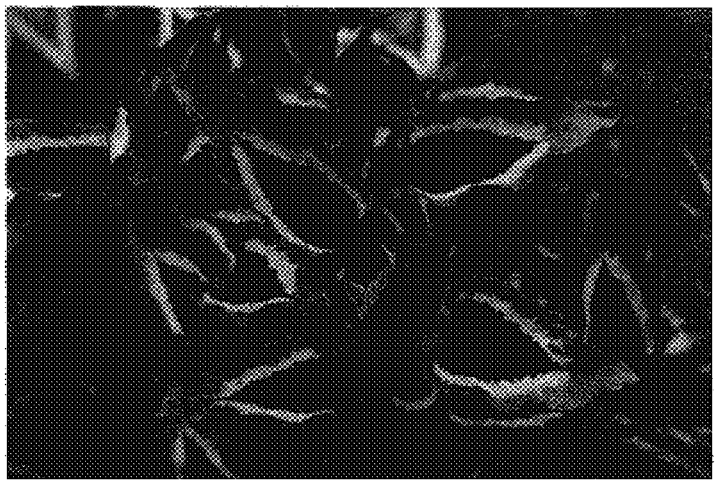
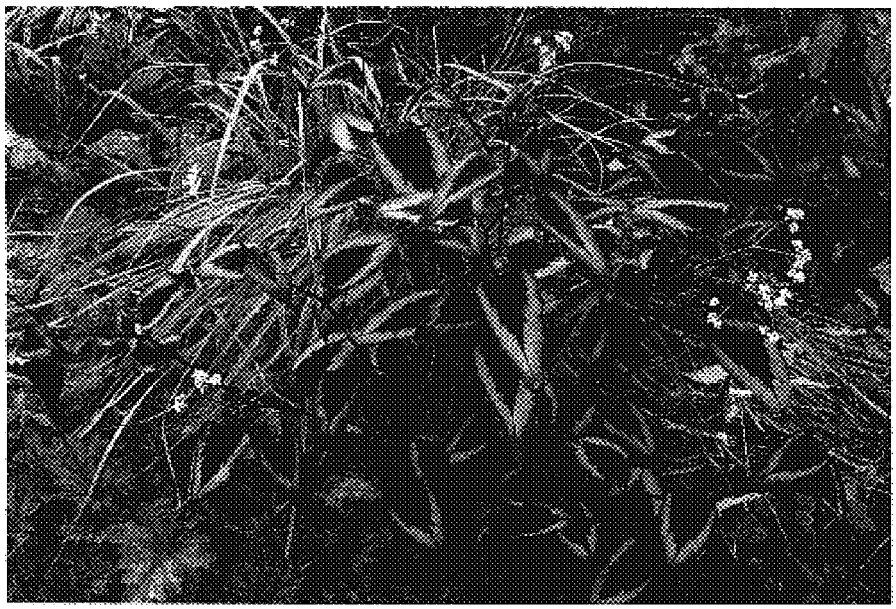
*Figure 2*
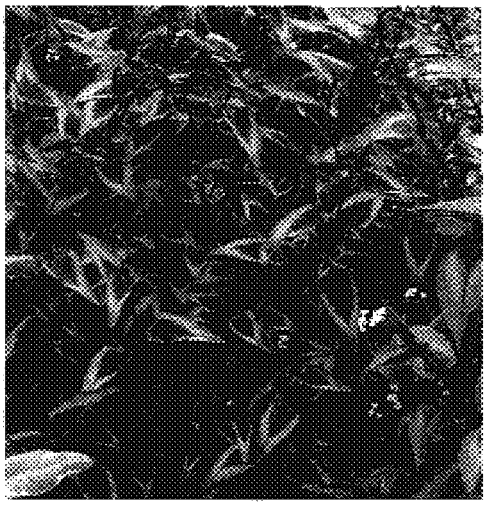
*Figure 3*